US00PP19572P2

(12) United States Plant Patent
Zornig

(10) Patent No.: US PP19,572 P2
(45) Date of Patent: Dec. 16, 2008

(54) *GUZMANIA* PLANT NAMED 'BEL-AIR'

(50) Latin Name: *Guzmania conifera*
Varietal Denomination: Bel-Air

(75) Inventor: Rolf Kurt Zornig, Sao Paulo (BR)

(73) Assignee: Altria Lab-plants, LLC, Homestead, FL (US)

( * ) Notice: Subject to any disclaimer, the term of this patent is extended or adjusted under 35 U.S.C. 154(b) by 0 days.

(21) Appl. No.: 12/011,387

(22) Filed: Jan. 25, 2008

(51) Int. Cl.
*A01H 5/00* (2006.01)

(52) U.S. Cl. ..... Plt./371

(58) Field of Classification Search ..... Plt./371
See application file for complete search history.

*Primary Examiner*—Annette H Para
(74) *Attorney, Agent, or Firm*—C. A. Whealy

(57) ABSTRACT

A new and distinct cultivar of *Guzmania* plant named 'Bel-Air', characterized by its compact, upright and outwardly arching growth habit; dark green-colored foliage; inflorescences held upright and above foliage on strong scapes; inflorescences with closely-spaced dark purple-colored primary bracts that are tipped with yellow; and long-lasting inflorescences that maintain good coloration for about four months in the interiorscape and about 20 to 30 weeks in the greenhouse.

2 Drawing Sheets

Botanical designation: *Guzmania conifera.*
Cultivar denomination: 'BEL-AIR'.

BACKGROUND OF THE INVENTION

The present invention relates to a new and distinct cultivar of *Guzmania,* botanically known as *Guzmania conifera* and hereinafter referred to by the name 'Bel-Air'.

The new *Guzmania* is a product of a planned breeding program conducted by the Inventor in Sao Paulo, Brazil. The objective of the breeding program is to create new *Guzmania* varieties having unique flower colors and enhanced postproduction longevity.

The new *Guzmania* originated from a cross-pollination made by the Inventor in January, 1999, in Sao Paulo, Brazil, of a proprietary section of *Guzmania conifera* identified as code number L#32, not patented, as the female, or seed, parent with a proprietary selection of *Guzmania conifera* identified as code number B#4, not patented, as the male, or pollen, parent. The new *Guzmania* was discovered and selected by the Inventor as a flowering plant within the progeny of the stated cross-pollination in a controlled environment in Sao Paulo, Brazil, in September, 2003.

Asexual reproduction of the new *Guzmania* by tissue culture in a controlled environment in Homestead, Fla., has shown that the unique features of this new *Guzmania* are stable and reproduced true to type in successive generations.

SUMMARY OF THE INVENTION

The cultivar Bel-Air has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bel-Air'. These characteristics in combination distinguish 'Bel-Air' as a new and distinct cultivar of *Guzmania:*

1. Compact, upright and outwardly arching growth habit.
2. Dark green-colored foliage.
3. Inflorescences held upright and above foliage on strong scapes.
4. Inflorescences with closely-spaced dark purple-colored primary (flower) bracts that are tipped with yellow.
5. Long-lasting inflorescences that maintain good coloration for about four months in the interiorscape and about 20 to 30 weeks in the greenhouse.

Plants of the new *Guzmania* can be compared to plants of the female parent selection in the following characteristics:

1. Plants of the new *Guzmania* are more compact than plants of the female parent selection.
2. Leaves of plants of the new *Guzmania* are darker green in color than leaves of plants of the female parent selection.
3. Plants of the new *Guzmania* and female parent selection differ in primary bract color as plants of the female parent selection have red-colored primary bracts.

Plants of the new *Guzmania* can be compared to plants of the male parent selection in the following characteristics:

1. Plants of the new *Guzmania* are more compact than plants of the male parent selection.
2. Leaves of plants of the new *Guzmania* are darker green in color than leaves of plants of the male parent selection.
3. Plants of the new *Guzmania* and male parent selection differ in primary bract color as plants of the male parent selection have red and yellow-colored primary bracts.

Plants of the new *Guzmania* can be compared to plants of the *Guzmania* cultivar Olympic, disclosed in U.S. Plant Pat. No. 10,787. In side-by-side comparisons conducted in Homestead, Fla., plants of the new *Guzmania* and the cultivar Olympic differed in the following characteristics:

1. Leaves of plants of the new *Guzmania* were darker in color than leaves of plants of the cultivar Olympic.
2. Plants of the new *Guzmania* and the cultivar Olympic differed in primary bract color as plants of the cultivar Olympic had yellow and orange-colored flowers bracts.

Plants of the new *Guzmania* can be compared to plants of the *Guzmania* cultivar Torch, disclosed in U.S. Plant Pat. No. 9,426. In side-by-side comparisons conducted in Homestead, Fla., plants of the new *Guzmania* and the cultivar Torch differed in the following characteristics:

1. Plants of the new *Guzmania* were more compact than plants of the cultivar Torch.
2. Plants of the new *Guzmania* and the cultivar Torch differed in primary bract color as plants of the cultivar Torch had orange and yellow-colored flowers bracts.

BRIEF DESCRIPTION OF THE PHOTOGRAPHS

The accompanying colored photographs illustrated the overall appearance of the new *Guzmania,* showing the colors as true as it is reasonably possible to obtain in colored reproductions of this type. Colors in the photographs may differ slightly from the color values cited in the detailed botanical description which accurately describe the colors of the new *Guzmania.*

The photograph on the first sheet comprises a side perspective view of a typical flowering plant of 'Bel-Air' grown in a container.

The photograph on the second sheet is a close-up view of a typical inflorescence of 'Bel-Air'.

DETAILED BOTANICAL DESCRIPTION

All color references are measured against The Royal Horticultural Society Colour Chart, 1995 Edition. Colors and numerical measurements are approximate as plant growth and development depends on environmental conditions and cultural practices such as light level and temperature, among others, without, however any variance in genotype.

Plants used for the aforementioned photographs and the following description were about 14 months old and grown in 15-cm containers in Homestead, Fla., during the spring in a polyethylene-covered greenhouse with day temperatures averaging 28° C., night temperatures averaging 20° C. and light levels about 1,600 foot-candles.

Botanical classification: *Guzmania conifera* cultivar Bel-Air.

Parentage:

*Female, or seed, parent.*—Proprietary selection of *Guzmania conifera* L#32, not patented.

*Male, or pollen, parent.*—Proprietary selection of *Guzmania conifera* B#4, not patented.

Propagation:

*Type.*—By tissue culture.

*Time to initiate roots on tissue-cultured plants.*—Summer: About 14 days at temperatures of 29° C. Winter: About 20 days at temperatures of 24° C.

*Time to produce a rooted tissue-cultured plant.*—Summer: About 110 days at 29° C. Winter: About 130 days at 24° C.

*Root description.*—Tough, fine and wiry; greenish white becoming dark brown with age.

*Rooting habit.*—Freely branching; moderately dense.

Plant description:

*General appearance.*—Compact, upright and outwardly arching plant habit. Basal rosette of outwardly curved, channeled, strap-like leaves affixed in tight spiral ranks around a very short central stem. Terminal inflorescence on an upright scape with emerges from the center of the basal rosette.

*Plant height, soil surface to top of inflorescence.*—About 45 cm.

*Plant diameter or spread.*—About 62 cm to 67 cm.

*Stem length.*—About 6 cm.

*Stem diameter.*—About 3 cm.

*Stem color.*—155D.

Foliage description:

*Arrangement.*—Basal rosette, spiral phyllotaxis; sessile.

*Quantity of leaves per plant.*—Plants typically produce about 30 to 35 leaves prior to inflorescence development.

*Shape.*—Ligulate.

*Apex.*—Acute.

*Margin.*—Entire.

*Length.*—About 36 cm to 42 cm.

*Width (flattened).*—About 3 cm to 3.8 cm; width at base, about 6.7 cm to 8 cm.

*Aspect.*—Blade, channeled; leaves curved outward over their length and downward towards the apex.

*Texture, upper and lower surfaces.*—Leathery, stiff; smooth, glabrous.

*Venation.*—Parallel.

*Leaf sheath.*—Not observed.

*Color.*—Developing and fully expanded leaves, upper surface: Darker than, but closest to 137A; towards the base, faintly tinged with 187A; sparse, faint, mostly marginal striations, 187A; leaf base, between 155D and 145D tinged with 199D. Developing and fully expanded leaves, lower surface: More green than 147A flushed with 187A; striations towards the base, 187A; leaf base, between 155D and 145D tinged with 174A. Venation, upper and lower surfaces: Similar to lamina.

Inflorescence description:

*Inflorescence form.*—Terminal inflorescences with showy primary (flower) bracts; inflorescences supported on erect and strong scapes.

*Fragrance.*—None detected.

*Inflorescence longevity.*—Inflorescences of the new *Guzmania* are very long-lasting; bract coloration is maintained for about four months in an interiorscape and about 20 to 30 weeks in the greenhouse. Inflorescences persistent.

*Natural flowering season and time to flower.*—Plants of the new *Guzmania* typically flower in the spring or summer 14 weeks after floral induction.

*Flowers.*—Arrangement: Single flowers emerge from underneath terminal (fertile) bracts and last about one day; one flower per terminal bract. Quantity per flower spike: About 95 flowers and flower buds. Unopened buds: Length: About 3.2 cm. Diameter: About 5 mm. Color: 5B. Corolla: Arrangement: Three petals, gamopetalous. Length: About 4.4 cm. Width: About 6 mm. Shape: Lanceolate. Apex: Obtuse. Color: 5B to 5C; color becoming closer to 163D with development. Calyx: Arrangement: Three sepals, gamosepalous. Length: About 2.4 cm. Width: About 5 mm. Shape: Lanceolate. Apex: Acute. Color: 155B.

*Reproductive organs.*—Stamens: Quantity per flower: Six. Filament length: About 6 mm. Filament diameter: About 1 mm. Filament color: 11D. Anther length: About 5.5 mm. Anther width: About 1 mm. Anther color: 11C. Pollen: None observed. Pistils: Stigma shape: Three-lobed. Stigma length: About 2 mm. Stigma diameter: Less than 1 mm. Stigma color: 2C. Style length: About 2.8 cm. Style diameter: Less than 1 mm. Style color: 10D. Ovary: Superior with three locules. Ovary length: About 9 mm. Ovary diameter: About 3 mm. Ovary color: 145D.

*Seed/fruit.*—Seed and fruit production has not been observed.

*Bracts.*—Terminal (fertile) bracts uppermost on inflorescence, subtended by primary bracts. Scape bracts lowermost and sheath the scape. Quantity per flower spike, terminal bracts: About 95. Quantity per flower spike, primary bracts: About 14. Quantity per flower spike, scape bracts: About 14. Shape, terminal bracts: Ovate in shape becoming narrower and more ligulate towards the apex of the inflorescence; apices, acute; margins, entire. Shape, primary bracts: Ovate; apices; acute; margins, entire. Shape, scape bracts: Ligulate; apices, acute; margins, entire. Length, terminal bracts: About 3.5 cm to 5.7 cm. Length, primary bracts: About 7.5 cm to 11 cm. Length, scape bracts: About 12 cm to 25 cm. Width, terminal bracts: About 0.9 mm to 1 cm. Width, primary bracts: About 2.8 cm to 3 cm. Width, scape bracts: About 3 cm to 3.8 cm. Texture, all bracts, upper and lower surfaces: Leathery, stiff; smooth, glabrous. Color: Terminal bracts, upper surface: 187C to 187D tinted with 158C; apices, 9C; towards the base, 150D. Terminal bracts, lower surface: More red than 187B to 187C; apices, 9C; towards the base, 150D. Primary bracts, upper surface: 187B to 187C; apices, 187A, occasionally tinged with 147A; towards the base, 145C. Primary bracts, lower surface: 187B; apices, 187A, occasionally tinged with 147A; towards the base, 145C tinged with 165B. Lower scape bracts, upper surface: Darker than 137A; towards the base, 137A flushed with 187A to 187B; base, 159C. Lower scape bracts, lower surface: Lighter than 147A flushed with 187A; towards the base; tinged with 175A. Upper scape bracts, upper surface: 147A flushed with 187A; towards the base and margins, 187B to 187C; at the base, 145C. Upper scape bracts, lower surface: 147A flushed with 187A; towards the base and margins, 187B to 187C; at the base, tinged with 175A.

*Scape.*—Strength: Strong. Aspect: Typically erect. Length: About 40 cm. Diameter: About 1.3 cm. Texture: Smooth, glabrous. Color: 145D.

Temperature tolerance: Plants of the new *Guzmania* have been observed to tolerate temperatures from about 6° C. to about 37° C.

Disease/pest resistance: Plants of the new *Guzmania* have not been observed to resistant to pathogens and pests common to *Guzmania*.

It is claimed:

1. A new and distinct *Guzmania* plant named 'Bel-Air' as illustrated and described.

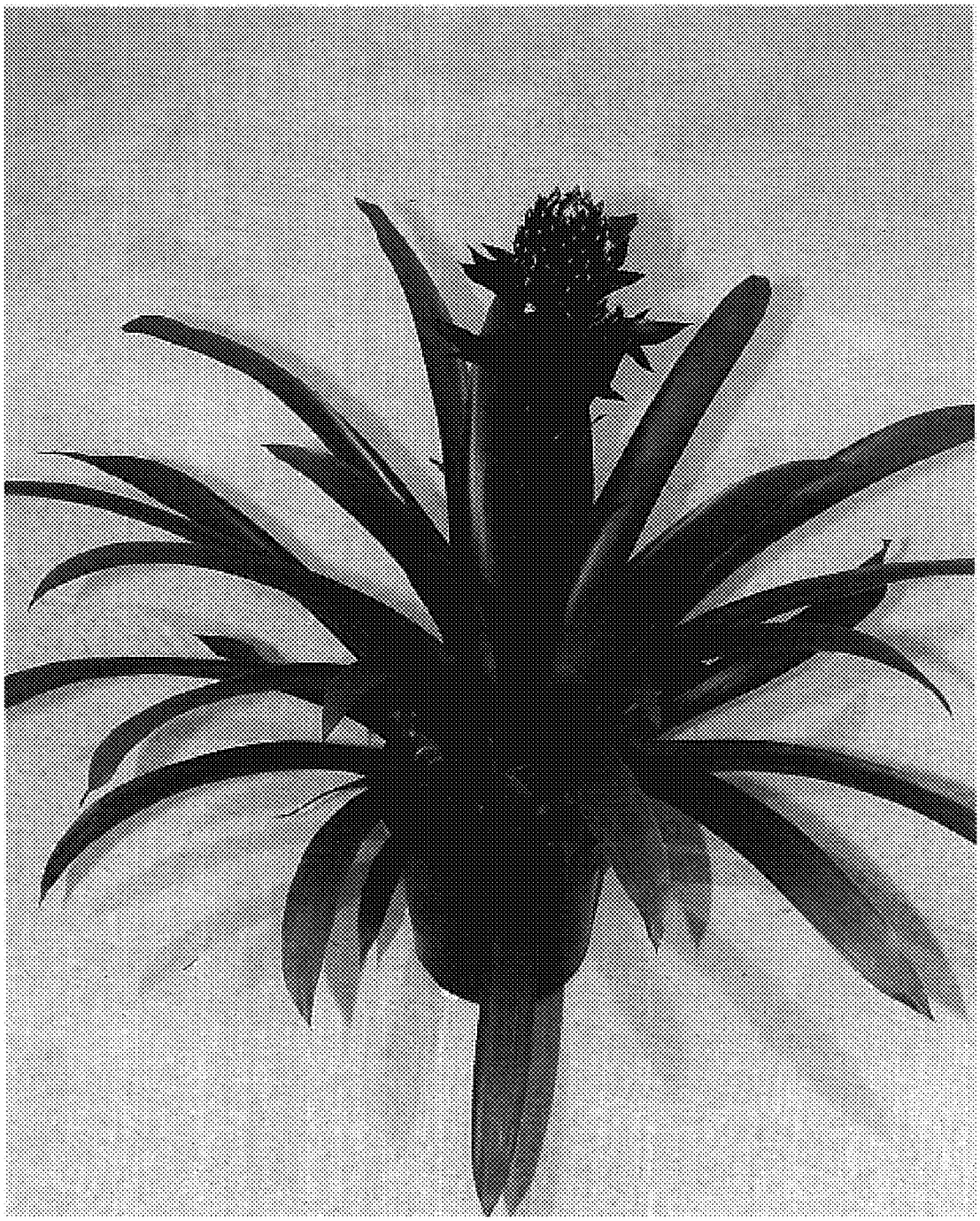

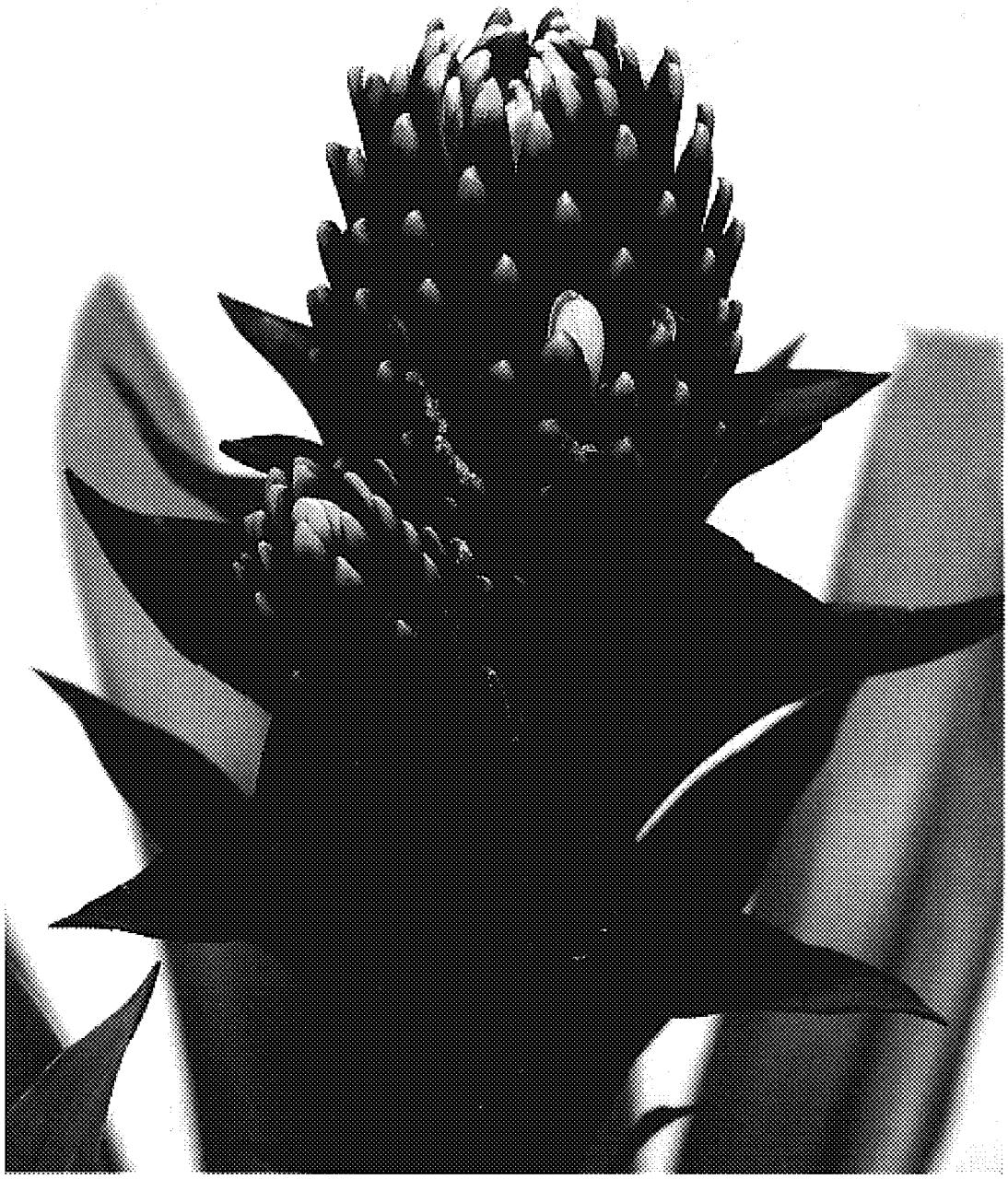

* * * * *